United States Patent
Pees et al.

(10) Patent No.: US 7,230,104 B2
(45) Date of Patent: Jun. 12, 2007

(54) FUNGICIDAL 5-PHENYL SUBSTITUTED 2-(CYANOAMINO) PYRIMIDINES

(75) Inventors: Klaus-Juergen Pees, Mainz (DE); Waldemar Pfrengle, Biberach (DE); Gavin Heffernan, Florence, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/186,087

(22) Filed: Jul. 22, 2005

(65) Prior Publication Data

US 2005/0282847 A1   Dec. 22, 2005

Related U.S. Application Data

(62) Division of application No. 10/615,352, filed on Jul. 9, 2003, now Pat. No. 6,943,252, which is a division of application No. 09/879,283, filed on Jun. 12, 2001, now Pat. No. 6,632,821.

(60) Provisional application No. 60/231,632, filed on Sep. 11, 2000, provisional application No. 60/211,262, filed on Jun. 13, 2000.

(51) Int. Cl.
*C07D 239/02*   (2006.01)

(52) U.S. Cl. .................. 544/317; 544/320; 544/321; 544/323; 544/324

(58) Field of Classification Search ............... 544/317, 544/320, 321, 323, 324
See application file for complete search history.

(56) References Cited

U.S. PATENT DOCUMENTS

| 4,438,117 A | 3/1984 | Cherkofsky | 424/251 |
|---|---|---|---|
| 4,504,482 A | 3/1985 | Lesher et al. | 514/275 |
| 4,847,258 A | 7/1989 | Sturm et al. | 514/274 |
| 4,906,401 A | 3/1990 | Dubal et al. | 252/299.61 |
| 4,906,752 A | 3/1990 | Mueller et al. | 544/318 |
| 5,366,657 A | 11/1994 | Illian et al. | 252/299.6 |
| 6,150,526 A | 11/2000 | Binggeli et al. | 546/139 |

FOREIGN PATENT DOCUMENTS

| EP | 0 257 605 | 8/1987 |
|---|---|---|
| EP | 0 284 008 | 3/1988 |
| EP | 0 295 370 | 3/1988 |
| EP | 0 613 900 | 9/1994 |
| GB | 2 227 090 | 10/1994 |
| WO | 85 00603 | 2/1985 |
| WO | 89 03416 | 4/1989 |
| WO | 91 11441 | 8/1991 |
| WO | 92 02513 | 2/1992 |
| WO | 95 35283 | 12/1995 |
| WO | 97 09311 | 3/1997 |
| WO | 98 38171 | 9/1998 |
| WO | 00 73278 | 12/2000 |

*Primary Examiner*—Deepak Rao
(74) *Attorney, Agent, or Firm*—Novak Druce & Quigg, LLP

(57) ABSTRACT

Pyrimidines of formula I

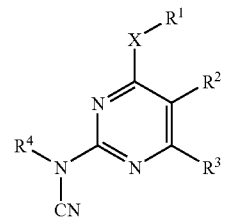

in which
$R^1$ represents hydrogen or alkyl, haloalkyl, alkenyl, alkynyl, alkadienyl, alkoxy, cycloalkyl, phenyl, or 5- or 6-membered heteroaryl or 5- or 6-membered heterocyclyl, containing one to four nitrogen atoms or one to three nitrogen atoms and one sulfur or oxygen atom, or tri-alkyl-silyl, formyl or alkoxy-carbonyl,
  wherein $R^1$ groups are unsubstituted or substituted as defined in the specification;
  $R^2$ represents phenyl, cycloalkyl or 5- or 6-membered heteroaryl, containing one to four nitrogen atoms or one to three nitrogen atoms and one sulfur or oxygen atom, which are unsubstituted or substituted;
  $R^3$ represents hydrogen, halogen or alkyl, alkoxy, alkylthio, alkylamino or dialkylamino; which are unsubstituted or substituted;
  $R^4$ represents hydrogen or alkyl, alkenyl or alkynyl; which are unsubstituted or substituted; and
  X represents O, S, $NR^5$ or a single bond, wherein $R^5$ represents hydrogen or alkyl; or
  $R^1$ and $R^5$ together with the interjacent nitrogen atom form a heterocyclic ring;
processes and intermediates for preparing these compounds, to compositions comprising them and to their use for controlling harmful fungi.

9 Claims, No Drawings

FUNGICIDAL 5-PHENYL SUBSTITUTED 2-(CYANOAMINO) PYRIMIDINES

This is a divisional application of application Ser. No. 10/615,352, filed Jul. 9, 2003, now U.S. Pat. No. 6,943,252, which is a divisional application of application Ser. No. 09/879,283, now U.S. Pat. No. 6,632,821, filed Jun. 12, 2001, which claims the benefit under 35 U.S.C. 119(e) of provisional applications 60/211,262, filed Jun. 13, 2000 and 60/231,632, filed Sep. 11, 2000. The entire disclosures of the aforementioned parent and provisional applications are hereby incorporated herein by reference.

The present invention relates to pyrimidines of formula I

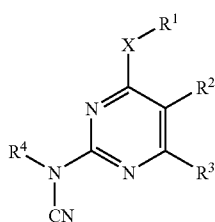

in which
$R^1$ represents hydrogen or
$C_1$–$C_{10}$-alkyl, $C_1$–$C_{10}$-haloalkyl, $C_2$–$C_6$-alkenyl, $C_2$–$C_6$-alkynyl, $C_4$–$C_8$-alkadienyl, $C_1$–$C_{10}$-alkoxy, $C_3$–$C_8$-cycloalkyl, phenyl, or
5- or 6-membered heteroaryl or 5- or 6-membered heterocyclyl, containing one to four nitrogen atoms or one to three nitrogen atoms and one sulfur or oxygen atom, or
tri-$C_1$–$C_6$-alkyl-silyl, formyl or $C_1$–$C_{10}$-alkoxycarbonyl;
wherein $R^1$ groups are unsubstituted or substituted by one to three groups $R^a$
$R^a$ halogen, nitro, cyano, hydroxy or
$C_1$–$C_{10}$-alkyl, $C_3$–$C_6$-cycloalkyl, $C_3$–$C_6$-cycloalkenyl, $C_1$–$C_{10}$-haloalkyl, $C_3$–$C_6$-halocycloalkyl, $C_1$–$C_{10}$-alkoxy, $C_1$–$C_{10}$-haloalkoxy, $C_1$–$C_{10}$-haloalkoxy, $C_1$–$C_6$-alkoxycarbonyl, tri-$C_1$–$C_4$-alkylsilyl, phenyl, halo- or dihalo-phenyl or 5- or 6-membered heteroaryl, containing one to four nitrogen atoms or one to three nitrogen atoms and one sulfur or oxygen atom;
$R^2$ represents phenyl, $C_3$–$C_6$-cycloalkyl or 5- or 6-membered heteroaryl, containing one to four nitrogen atoms or one to three nitrogen atoms and one sulfur or oxygen atom, which are unsubstituted or substituted by one to three groups $R^a$;
$R^3$ represents hydrogen, halogen or
$C_1$–$C_{10}$-alkyl, $C_1$–$C_{10}$-alkoxy, $C_1$–$C_{10}$-alkylthio, $C_1$–$C_{10}$-alkylamino or di-$C_1$–$C_{10}$-alkylamino; which are unsubstituted or substituted by one to three groups $R^a$;
$R^4$ represents hydrogen or
$C_1$–$C_{10}$-alkyl, $C_2$–$C_6$-alkenyl or $C_2$–$C_6$-alkynyl; which are unsubstituted or substituted by one to three groups $R^a$; and
X represents O, S, $NR^5$ or a single bond, wherein $R^5$ represents hydrogen or $C_1$–$C_{10}$-alkyl; or
$R^1$ and $R^5$ together with the interjacent nitrogen atom form a heterocyclic ring.

Moreover, the invention relates to processes and intermediates for preparing these compounds, to compositions comprising them and to their use for controlling harmful fungi.

In vestn. Slov. Kem. Drus. (1986), 33(3), 353-66 (ISSN: 0560-3110, CAN 107:39701) it is disclosed that the reaction of N-pyrimid-2-ylformamide oxires with N,N-dimethylformamide diethyl acetal yields 2-(N-cyano-N-ethylamino)pyrimidines. In J. Org. Chem. 39 (9) 1256–1252 (1974) N-glycosylated 2-(N-cyanoamino) pyrimidines are disclosed and in U.S. Pat. No. 4,711,959 a process for the preparation of 2-(N-cyanoamino) pyrimidines is described.

It is an object of the present invention to provide fungicidal compounds having improved activity.

We have found that this object is achieved by the compounds defined at the outset. Furthermore, we have found processes for their preparation, compositions comprising them and methods for controlling harmful fungi using the compounds I.

Compounds of formula I wherein $R^4$ is an optionally substituted alkyl, alkenyl or alkynyl group as defined above may be obtained by treating a compound of the formula II

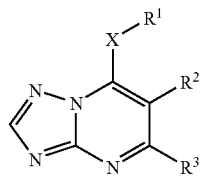

in which $R^1$ through $R^3$ and X are as defined in formula I; with a strong base and an alkylation agent of formula III

   III in which $R^4$ is $C_1$–$C_6$-alkyl, $C_1$–$C_6$-alkenyl or $C_1$–$C_6$-alkynyl; which are unsubstituted or substituted by one to three groups $R^a$, and Y represents a nucleophilic replaceable leaving group, preferably a halogen atom, in particular a iodine atom.

Compounds of formula II are known for example from U.S. Pat. No. 5,593,996, WO-A 98/46608, FR-A 2,765,875, WO-A 99/41255 or WO-A 99/48893.

The reaction between the triazolopyrimidines of formula II, the strong base and the alkylation agent of formula III is preferably carried out in the presence of an inert solvent. Suitable solvents include ethers, such as dioxane, diethyl ether and tetrahydrofuran, halogenated hydrocarbons such as dichloromethane, amides, such as dimethylformamide or N-methylpyrrolidone and aromatic hydrocarbons, for example toluene or mixtures of these solvents. The reaction is suitably carried out at a temperature in the range from –78° C. to 100° C., the preferred reaction temperature is from 10° C. to 80° C., particular at ambient temperature.

Suitable strong bases include metal hydrides, such as sodium hydride, potassium hydride or calcium hydride, and metal amides, such as sodium amide, potassium amide, lithium diisopropylamide or potassium hexamethyldisilazide, and metal alkanes such as methyllithium, n-butyllithium or tert-butyllithium.

Furthermore, the compounds of formula I wherein $R^4$ is an optionally substituted alkyl, alkenyl or alkynyl group may be prepared by reacting a N-pyrimid-2-ylformamide oxime of formula IV

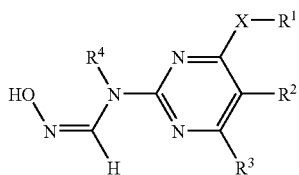

in which $R^1$ through $R^3$ and X are as defined in formula I; with a N,N-dimethylformamide dialkyl acetate of formula V

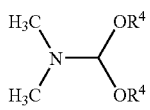

in which $R^4$ is $C_1$–$C_6$-alkyl, $C_1$–$C_6$-alkenyl or $C_1$–$C_6$-alkynyl; which are unsubstituted or substituted by one to three groups $R^a$.

The reaction between the compounds of formula IV and the compounds of formula V can be carried out analogously to the reaction described in Vestn. Slov. Kem. Drus. (1986), 33(3), 353–66.

Compounds of formula I wherein $R^4$ is hydrogen can preferably be prepared by treating sulfones of formula VI

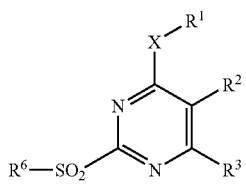

in which $R^1$ through $R^3$ and X are as defined in formula I and $R^6$ is $C_1$–$C_6$-alkyl or $C_1$–$C_6$-haloalkyl; with cyanamide or with a metal salt of cyanamide. The use of a base and/or a solvent can be advantageous.

This process is preferably carried out in the presence of an inert solvent. Suitable solvents include aromatic hydrocarbons, such as, for example toluene or xylene, chlorinated hydrocarbons, such as, for example methylene chloride, chloroform, a chlorobenzene, ketones, such as, for example acetone, methyl ethyl ketone, methyl isopropyl ketone or methyl isobutyl ketone, nitriles, such as, for example acetonitrile or propionitrile ethers, such as, for example diethyl ether, diisopropyl ether, methyl tert-butylether, dimethoxyethane, tetrahydrofuran or dioxane, amides, such as, for example, dimethylacetamide or diethylacetamide, sulfoxides, such as, for example dimethylsulfoxide or sulfolane, or mixtures thereof.

The use of a base can be advantageous in this reaction. Suitable bases include alkali metal hydrides and earth alkaline metal hydrides, such as, for example, sodium, potassium or calcium hydrides, alkali metal hydroxides and alkaline earth metal hydroxides, such as, for example, sodium, potassium or calcium hydroxides, alkali metal carbonates and alkaline earth metal carbonates, such as, for example sodium carbonate, potassium carbonate or calcium carbonate, alkali metal bicarbonates and alkaline earth metal bicarbonates, such as sodium bicarbonate, potassium bicarbonate or calcium bicarbonate, metal amides, such as, for example sodium amide, potassium amide, lithium diisopropylamide or potassium hexamethyldisilazide, metal alkanes, such as for example methyl lithium, n-butyl lithium or tert-butyl lithium or aprotic amines, such as, for example pyridine, tributylaine, N,N-dimethylbenzylamine or diazobicycloundecene.

Various qualities of cyanamide may be employed for the process. The use of an aqueous solution of cyanamide may be preferred for practical reasons. The use of metal salts of cyanamide, potassium cyanamide, dipotassium cyanamide or calcium cyanamide is also possible.

Dependant an the used cyanamide or salt of, cyanamide and dependant on the base an appropriate solvent is employed.

The reaction is suitable carried out at a temperature in the range from –78° C. to reflux temperature, the preferred reaction temperature is from 0° C. to 150° C., particular at ambient temperature.

In general 1 to 3 equivalents, preferably 1.5 to 2.5 equivalents of base are employed per equivalent of sulfone of the formula VI.

Generally 2 to 6 equivalents, preferably 3 to 5 equivalents of cyanamide or salt of cyanamide are employed per equivalent of the sulfone of the general formula VI.

Compounds of formula I wherein $R^4$ is $C_1$–$C_6$-alkyl, $C_1$–$C_6$-alkenyl or $C_1$–$C_6$-alkynyl which are unsubstituted or substituted by one to three groups $R^a$ may be prepared by alkylation of compounds of formula I wherein $R^4$ is hydrogen with an alkylation agent of formula III.

The use of a base can be advantageous in this reaction. Suitable bases include alkali metal hydrides and earth alkaline metal hydrides, such as, for example, sodium, potassium or calcium hydrides, alkali metal hydroxides and alkaline earth metal hydroxides, such as, for example, sodium, potassium or calcium hydroxides, alkali metal carbonates and alkaline earth metal carbonates, such as, for example sodium carbonate, potassium carbonate or calcium carbonate, alkali metal bicarbonates and alkaline earth metal bicarbonates, such as sodium bicarbonate, potassium bicarbonate or calcium bicarbonate, metal amides, such as, for example sodium amide, potassium amide, lithium diisopropylamide or potassium hexamethyldisilazide, metal alkanes, such as for example methyl lithium, n-butyl lithium or tert-butyl lithium or aprotic amines, such as, for example pyridine, tributylaine, N,N-dimethylbenzylamine or diazobicycloundecene.

The alkylation is preferably carried out in the presence of an inert solvent. Suitable solvents include aromatic hydrocarbons, such as, for example toluene or xylene, chlorinated hydrocarbons, such as, for example methylene chloride, chloroform, a chlorobenzene, ketones, such as, for example acetone, methyl ethyl ketone, methyl isopropyl ketone or methyl isobutyl ketone, nitrites, such as, for example acetonitrile or propionitrile ethers, such as, for example diethyl ether, diisopropyl ether, methyl tert-butylether, dimethoxyethane, tetrahydrofuran or dioxane, amides, such as, for example, dimethylacetamide or diethylacetamide, sulfoxides, such as, for example dimethylsulfoxide or sulfolane, or mixtures thereof.

The reaction is suitably carried out at a temperature in the range from –78° C. to reflux temperature, the preferred reaction temperature is 0° C. to 150° C., particular ambient temperature.

In general 0.8 to 5 equivalents, preferably 0.8 to 4.5 equivalents of the alkylation agent of the formula III are employed per equivalent of the compound of formula I.

Usually 0.8 to 3 equivalents, preferably 0.8 to 2.5 equivalents of base are employed per equivalent of the compound of formula I.

It is also possible to prepare compounds of formula I wherein $R^4$ is $C_1$–$C_6$-alkyl, $C_1$–$C_6$-alkenyl or $C_1$–$C_6$-alkynyl which are unsubstituted or substituted by one to three groups $R^a$ by reacting a sulfone of formula VI

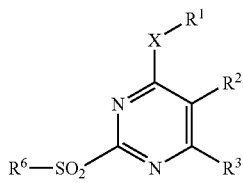

VI in which $R^1$ through $R^3$ and X are as defined in formula I and $R^6$ is $C_1$–$C_6$-alkyl or $C_1$–$C_6$-haloalkyl; with an alkylated cyanamide of formula VII

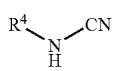

VII wherein $R^4$ is $C_1$–$C_6$-alkyl, $C_1$–$C_6$-alkenyl or $C_1$–$C_6$-alkynyl which are unsubstituted or substituted by one to three groups $R^a$. The use of a base and/or a solvent can be advantageous.

Suitable bases and solvents are such as listed at the reaction with cyanamide.

The reaction is suitable carried out at a temperature in the range of from –78° C. to reflux temperature, the preferred reaction temperature is from 0° C. to 150° C., particular at ambient temperature.

The reaction is in general carried out under usual pressure.

In general 1 to 3 equivalents preferably 1.5 to 2.5 equivalents of base are employed per equivalent of the sulfone of formula VI.

Usually 2 to 6 equivalents, preferably 3 to 5 equivalents of alkylated cyanamide of formula VII are employed per equivalents of the sulfone of formula VI.

Sulfones of the formula VI are obtained by reacting 2-thiopyrimidinederivatives of the formula VIII

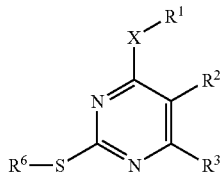

VIII in which the variables are as defined in formula VI; with oxidizing agents, such as, for example m-chloroperbenzoic acid, per acetic acid, trifluoro per acetic acid, chlorine water, hypochorous acid or metal salt solutions thereof in water or hydrogen peroxide, if appropriate in presence of a catalyst, such as for example wolframate.

If appropriate solvents, such as for example, methylene chloride, chloroform, carbontetrachloride, 1,2-dichloroethane or chlorobenzene are used at temperatures of –20° C. to reflux.

The 2-thiopyrimidine derivatives of the formula VIII may be obtained when 6-halo-2-thiopyrimidines of formula IX

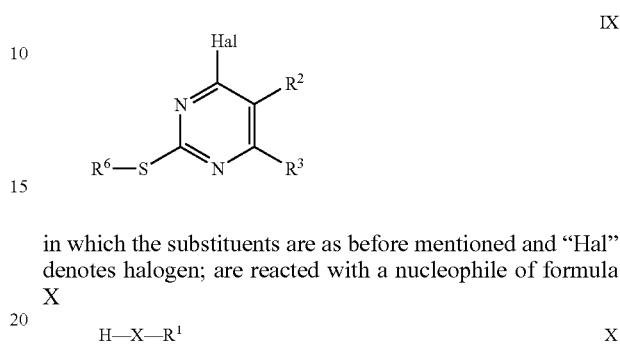

in which the substituents are as before mentioned and "Hal" denotes halogen; are reacted with a nucleophile of formula X

X wherein $R^1$ and X are as defined in formula I, if appropriate in the presence of a suitable base and if appropriate in an organic solvent. The solvents and bases employed are similar to those mentioned for the preparation of the compounds of formula I.

6-halo-2-thiopyrimidines of formula IX are known in the art or may be prepared according following reaction sequence:

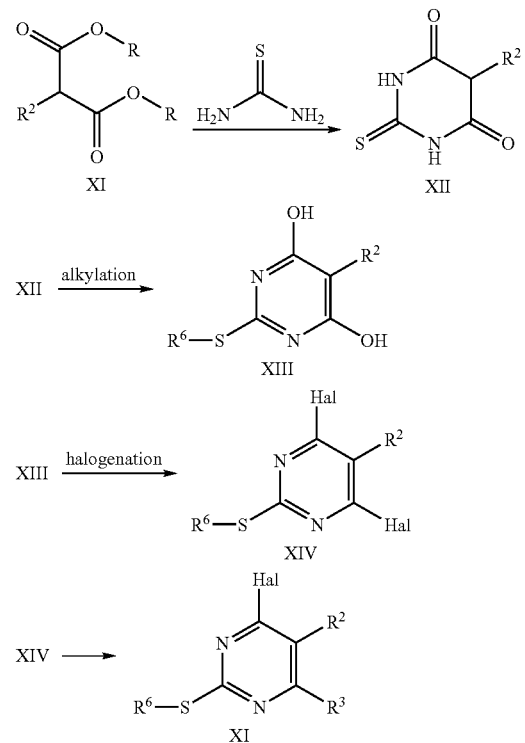

($R^2$, $R^3$ and $R^6$ are as defined above and R is an alkyl group) The reaction conditions are in general known in the art.

Base catalyzed reaction of dialkylmalonate with thiourea affords 2-thiobarbituric acid XII which may be selectively alkylated on sulfur to yield XIII.

Halogenation, preferably chlorination or bromination, especially chlorination, with for example phophorous oxychloride or phosphorous oxybromide in the presence of a tertiary amine base then affords the dihalo derivative XIV.

Subsequent introduction of the radical $R^3$, if appropriate, via nucleophilic substitution affords the 6-halo-2-thiopyrimidine of formula IX Sulfones of formula VI and 2-thiopyrimidine derivatives of formula VIII are novel.

In the symbol definitions given in the formulae above, collective terms were used which generally represent the following substituents:

halogen: fluorine, chlorine, bromine and iodine;

$C_1$–$C_6$-alkyl and the alkyl moieties of $C_1$–$C_6$-alkoxy, $C_1$–$C_6$-alkylthio, $C_1$–$C_6$-alkylamino, di-$C_1$–$C_6$-alkylamine or $C_1$–$C_6$-alkoxycarbonyl: saturated, straight-chain or branched hydrocarbon radicals having 1 to 6 carbon atoms, preferably $C_1$–$C_4$-alkyl, such as methyl, ethyl, propyl, 1-methylethyl, butyl, 1-methylpropyl, 2-methylpropyl, 1,1-dimethylethyl; or pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; preferably ethyl or methyl;

$C_1$–$C_6$-haloalkyl and the haloalkyl moieties of $C_1$–$C_6$-haloalkoxy: straight-chain or branched alkyl groups having 1 to 6 carbon atoms (as mentioned above), where the hydrogen atoms in these groups may be partially or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl; preferably 2,2,2-trifluoroethyl or 1,1,1-trifluoroprop-2-yl;

$C_3$–$C_8$-cycloalkyl: monocyclic, saturated hydrocarbon radicals having 3 to 6 or 8 carbon ring members, for example cyclopropyl, cyclobutyl, cyclopentyl, cyclohexyl, cycloheptyl and cyclooctyl, preferably 5 to 7 carbon atoms, in particular cyclopentyl being optionally substituted by one or more halogen atoms, nitro, cyano, $C_1$–$C_6$-alkyl or $C_1$–$C_6$-alkoxy.

$C_2$–$C_4$-alkenyl: unsaturated, straight-chain or branched hydrocarbon radicals having 2 to 4 carbon atoms and a double bond in any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl; preferably allyl or 2-methylallyl.

$C_2$–$C_4$-haloalkenyl and the haloalkenyl moieties of $C_2$–$C_4$-haloalkenyloxy: unsaturated, straight-chain or branched hydrocarbon radicals having 2 to 4 carbon atoms and a double bond in any position (as mentioned above), where the hydrogen atoms in these groups may be partially or fully replaced by halogen atoms as mentioned above, in particular by fluorine, chlorine and bromine;

$C_2$–$C_4$-alkynyl: straight-chain or branched hydrocarbon radicals having 3 to 4 carbon atoms and a triple bond in any position, for example ethynyl, 1-propynyl, 2-propynyl, 1-butynyl, 2-butynyl, 3-butynyl and 1-methyl-2-propynyl;

$C_3$–$C_4$-haloalkynyl and the haloalkynyl moieties of $C_2$–$C_4$-haloalkynyloxy: unsaturated, straight-chain or branched hydrocarbon radicals having 2 to 4 carbon atoms and a triple bond in any position (as mentioned above), where the hydrogen atoms in these groups may be partially or fully replaced by halogen atoms as mentioned above, in particular by fluorine, chlorine and bromine;

5-membered heteroaryl, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl; preferred hetaryl moieties are pyridyl, pyrimidyl, pyrazolyl or thienyl.

5- or 6-membered heterocyclyl, containing one to four nitrogen atoms or one to three nitrogen atoms and one sulfur or oxygen atom, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4- dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydro-triazin-2-yl and 1,2,4-hexahydrotriazin-3-yl; preferred heterocyclyl groups are pyrrolidinyl, pyrazolidinyl, piperidinyl, piperazinyl or morpholin-4-yl.

The particularly preferred embodiments of the intermediates with respect to the variables correspond to those of the radicals $R^1$, $R^2$, $R^3$ and $R^4$ of formula I.

With respect to their intended use, preference is given to pyrimidines of formula I having the following substituents, where the preference is valid in each case on its own or in combination:

Compounds of formula I are preferred wherein $R^1$ denotes $C_3$–$C_{10}$-alkyl, $C_3$–$C_8$-cycloalkyl, $C_3$–$C_8$-cycloalkyl-$C_1$–$C_6$-alkyl, $C_1$–$C_{10}$-haloalkyl or phenyl being optionally substituted by one to three halogen atoms or $C_1$–$C_{10}$-alkyl or $C_1$–$C_{10}$-alkoxy.

Furthermore, particular preference is given to compounds I in which $R^1$ is $C_1$–$C_{10}$-haloalkyl, preferably polyfluorinated alkyl, in particular 2,2,2-trifluoroethyl, 2-(1,1,1-trifluoropropyl) or 2-(1,1,1-trifluorobutyl).

Likewise, particular preference is given to compounds I in which $R^1$ denotes optionally substituted $C_3$–$C_8$-cycloalkyl, preferably cyclopentyl or cyclohexyl.

Moreover, particular preference is given to compounds I in which $R^2$ represents phenyl being substituted by 2 or 3 substituents. Most preferred at least one of these substituents is attached in the 2-position with respect to the point of attachment to the pyrimidine moiety. Such substituents preferably include halogen or alkoxy.

Furthermore, particular preference is given to compounds I in which $R^2$ represents a phenyl group of formula

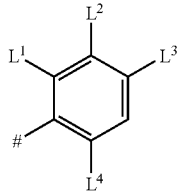

wherein $L^1$ through $L^4$ each independently represent hydrogen, fluorine, chlorine or methoxy, in particular $L^1$ represents fluorine or chlorine, $L^2$ and $L^4$ each independently represent hydrogen, fluorine or chlorine, and $L^3$ represents hydrogen, fluorine, chlorine or methoxy.

Particular preference is given to compounds of formula I in which $R^3$ is chlorine.

Besides, particular preference is given to compounds I in which $R^4$ represents hydrogen, $C_1$–$C_6$-alkyl, $C_2$–$C_6$-alkenyl or $C_2$–$C_6$-alkynyl; or phenyl-$C_1$–$C_4$-alkyl, wherein the phenyl ring may be substituted by one or two halogen atoms.

Likewise, particular preference is given to compounds I in which $R^4$ is hydrogen, $C_1$–$C_6$-alkyl or benzyl, especially $C_1$–$C_6$-alkyl.

Particular preference is given to compounds I in which X is $NR^5$ and $R^5$ is hydrogen, $C_1$–$C_{10}$-alkyl or $C_1$–$C_{10}$-haloalkyl, in particular hydrogen.

Besides, particular preference is given to compounds I in which $R^5$ represents $C_1$–$C_6$-alkyl, especially hydrogen or methyl.

Particular preference is also given to compounds I in which X represent $NR^5$ and $R^1$ together with the interjacent nitrogen atom form an optionally substituted heterocyclic ring, preferably an optionally substituted 3- to 7-membered heterocyclic ring, in particular a pyrrolidine, piperidine, tetrahydropyridine, in particular 1,2,3,6-tetrahydropyridine or azepane ring which is optionally substituted by one or more $C_1$–$C_{10}$-alkyl groups.

Most preferred are the compounds of formula IA

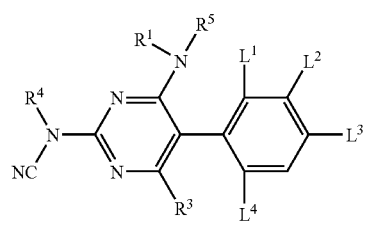

in which $R^1$ to $R^5$ have the meaning given in formula I, $L^1$ is F or Cl, $L^2$ and $L^4$ each independently are H, F or Cl, and $L^3$ is H, F, Cl or $OCH_3$.

Likewise, most preferred are the compounds wherein $R^3$ is chlorine, X is NH, $R^4$ is $C_1$–$C_6$-alkyl, $C_2$–$C_6$-alkenyl or $C_2$–$C_6$-alkynyl, especially $C_1$–$C_6$-alkyl, $R^2$ represents phenyl optionally substituted by one or more fluorine and/or chlorine atoms and/or methoxy groups.

Particularly preferred are following compounds of formula IA:

| $R^1$ | $R^5$ | $R^3$ | $R^4$ | $L^1$ | $L^2$ | $L^3$ | $L^4$ |
|---|---|---|---|---|---|---|---|
| $CH(CH_3)CF_3$ | H | Cl | $CH_3$ | F | H | F | F |
| $CH(CH_3)CF_3$ | H | Cl | $(CH_2)_3CH_3$ | F | H | F | F |
| $CH(CH_3)_2$ | H | Cl | $CH_3$ | F | H | F | F |
| c-$C_3H_5$ | H | Cl | $CH_3$ | F | F | H | F |
| azepan-1-yl | H | Cl | $CH_3$ | H | F | H | F |
| $(CH_2)_2CH(CH_3)(CH_2)_2$ | | Cl | $CH_3$ | F | H | H | Cl |
| $CH(CH_3)CH_2CH_3$ | H | Cl | $CH_3$ | F | H | H | Cl |
| $(CH_2)_2CH(CH_3)(CH_2)_2$ | | Cl | $CH_3$ | F | H | F | F |
| $CH(CH_3)CF_3$ | H | Cl | $CH_3$ | F | H | F | F |

Included in the scope of the present Invention are (R) and (S) isomers of compounds of general formula I having a chiral center and the racemates thereof, and salts, N-Oxides and acid addition compounds.

The compounds according to formula I are superior through their valuable fungicidal properties, in particular their enhanced systemicity. For example, they can be used in agriculture or related fields for the control of phytopathogenic fungi such as

*Alternaria solani, Botrytis cinerea, Cercospora beticola, Cladosporium herbarum, Corticium rolfsi, Erysiphe graminis, Helminthosporium tritici repentis, Lepfosphaeria nodorum, Micronectriella nivalis, Monilinia fructigena, Mycosphaerella ligulicola, Mycosphaerella pinodes, Rhizoctonia solani, Sclerotinia sclerotiorum, Uncinula necator* and *Venturia inaequalis*, in particular *Pyricularia oryzae, Rhizoctonia solani* and *Venturia inaequalis*. The compounds of formula I according to the invention possess a high fungicidal activity within a wide concentration range.

Due to excellent activity, the compounds of formula I may be used in cultivation of all plants where infection by phytopathogenic fungi is not desired, e.g. cereals, solanaceous crops, vegetables, legumes, appies, vine.

The Invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present Invention. It is also envisaged that different isomers or mixtures of isomers may have different levels or spectra of activity and thus compositions may comprise individual isomers or mixtures of isomers.

A composition according to the Invention preferably contains from 0.5% to 95% by weight (w/w) of active ingredient.

A carrier in a composition according to the Invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into e.g. emulsion concentrates, solutions, oil in watet emulsions, wettable powders, soluble powders, suspension concentrates, dusts, granules, watet dispersible granules, micro-capsules, gels, tablets and other formulation types by well established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be Chosen like the compositions according to the desired objectives and the given circumstances.

Solvents may be aromatic hydrocarbons, e.g. Solvess® 200, substituted naphthalenes, phthalic acid esters, such as dibutyl or dioctyl phthalate, aliphatic hydrocarbons, e.g. cyclohexane or Paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and watet. Mixtures of different liquids are often suitable.

Solid carriers, which may be used for dusts, wettable powders, watet dispersible granules, or granules, may be mineral fillers, such as calcite, talc, kaolin, montmorillonite or attapulgite. The physical properties may be improved by addition of highly dispersed silica gel or Polymers. Carriers for granules may be porous material, e.g. pumice, kaolin, sepiolite, bentonite; nonsorptive carriers may be calcite or sand. Additionally, a multitude of pregranulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the Invention is a surfactant. For example, the composition may contain at two or more carriers, at least one of which is a surfactant.

Surfactants may be nonionic, anionic, cationic or zwitterionic substances with good dispersing, emulsifying and wetting properties depending an the nature of the compound according to general formula I to be formulated. Surfactants may also mean mixtures of individual surfactants.

The compositions of the Invention may for example be formulated as wettable powders, water dispersible granules, dusts, granules, tablets, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stikkers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, nonsedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and watet or an organic liquid in which the active ingredient is substantially insoluble; certain organic solids or inorganic salis may be present dissolved in the formulation to assist in preventing sedimentation and crystalization or as antifreeze agents for water. Aqueous dispersions and emulsions, for example compositions obtained by diluting the formulated product according to the Invention with watet, also lie within the scope of the invention.

Of particular interest in enhancing the duration of the protective activity of the compounds of this Invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological actively of an active ingredient but is not itself significantly biologically active. The adjuvant can Bither be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the Invention are:

Emulsion Concentrate (EC)

| | | |
|---|---|---|
| Active Ingredient | Compound of Example 5 | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A[2] (mixture of $C_9$–$C_{10}$-aromatic hydrocarbons) | to 1000 ml |

Suspension Concentrate (SC)

| | | |
|---|---|---|
| Active Ingredient | Compound of Example 5 | 50% (w/v) |
| Dispersing agent | Soprophor ® FL[3] (polyoxyethylene polyaryl phenyl ether phosphate amine satt) | 3% (w/v) |
| Antifoaming agent | Rhodorsil ® 422[3] (nonionic aqueous emulsion of polydimethylsiloxanes) | 0.2 (w/v) |
| Structure agent | Kelzan ® S[4] (Xanthan gum) | 0.2 (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1 (w/v) |
| Water | | to 1000 ml |

Wettable Powder (WP)

| | | |
|---|---|---|
| Active Ingredient | Compound of Example 7 | 60% (w/w) |
| wetting agent | Atlox ® 4995[1] (polyoxyethylene alkyl ether) | 2% (w/w) |
| Dispersing agent | Witcosperse ® D-60[6] (mixture of sodium salts of condensed naphthalene suffonic acid and alkylarylpolyoxy acetates | 3% (w/w) |
| Carrier/Filter | Kaolin | 35% (w/w) | water Dispersible Granules (WG)

| | | |
|---|---|---|
| Active Ingredient | Compound of Example 7 | 50% (w/w) |
| Dispersing/Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) Antifoaming agent Rhodorsil ® EP 6703[3] (encapsulated silicone) | 2% (w/w) 1% (w/w) |
| Disintegrant | Agrimer ® ATF') (cross-linked homopolymer of N-vinyl-2 pyrrolidone) | 2% (w/w) |
| Carrier 1 Filter | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can be applied to the plants or their environment simultaneous with or in succession with other active substances. These other active substances can be Bither fertilisers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms. repellents of birds and animals, and plant growth regulators, or mixtures of several of these preparations, if appropriate together with other carrier substances conventionally used in the art of formulation, surfactants or other additives which promote application.

Furthermore, the other pesticide can have a synergistic effect and the pesticidal activity of the compound of formula I.

The other fungicidal compound can be, for example, one which is also capable of combating diseases of cereals (e.g. wheat) such as those caused by *Erysiphe, Puccinia, Septoria, Gibberella* and *Relminthosporium* spp., seed and soil Borne diseases and downy and powdery mildews an eines, early and late blight an solanaceous crops, and powdery mildew and scab an apples etc. These mixtures of fungicides can have a broader spectrum of activity than the compound of general formula I alone. Furthermore, the other fungicide can have a synergistic effect an the fungicidal activities of the compound of formula I.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenoxanil, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetylaluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoximmethyl, mancozeb, maneb, mepanipyrim, mepronil, metalaxyl, metconazole, methfuroxam, MON 65500, myclobutanil, neoasozin, nicket dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polgram, probenazole, prochloraz, procymidone, propamocarb, propiconazole, propineb, pyraclostrobin, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

In addition, the co-formulations according to the Invention mag contain at least one compound of formula I and any of the following classes of biological control agents such as viruses, bacteria, nematodes, fungi, and other microorganisms which are suitable to control insects, weeds or plant diseases or to induce holt resistance in the plants. Examples of such biological control agents are: *Bacillus thuringiensis, Verticillium lecanii, Autographica californica NPV, Beau-* varia bassiana, Ampelomyces quisqualis, Bacilis subtilis, Pseudomonas chlororaphis, Pseudomonas fluorescens, Steptomyces griseoviridis and Trichoderma harzianum.

Moreover, the co-formulations according to the Invention mag contain at least one compound of formula I and a chemical agent that induces the systemic acquired resistance in plants such as for example isonicotinic acid or derivatives thereof, 2,2-dichloro-3,3-dimethylcyclopropanecarboxylic acid or BION.

The compounds of formula I can be mixed with soil, peat or other rooting media for the protection of the plants against seedBorne, soilborne or foliar fungal diseases.

The Invention still further provides the use as a fungicide of a compound of the formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present Invention is of wide applicability in the protection of crop and ornamental plants against fungal attack. Typical crops which may be protected include eines, grain crops such as wheat and barley, rice, sugar Beet, top fruit, peanuts, potatoes, vegetables and tomatoes. The duration of the protection is normally dependent an the individual compound selected, and also a variety of external factors, such as climate, whose Impact is normally mitigated by the use of a suitable formulation.

SYNTHESIS EXAMPLES

With due modification of the starting compounds, the protocols shown in the synthesis examples below were used for obtaining further compounds I. The resulting compounds, together with physical data, are listed in the Tables which follow.

Example 1

Preparation of 2-(N-cyano-N-methylamino)-4-chloro-5-(2,4,6-trifluorophenul)-6-(1,1,1-trifluoro-prop-2-ylamino)-pyrimidine A mixture of 5-chloro-6-(2,4,6-trifluorophenyl)-7-(1,1,1-trifluoroprop-2-ylamino)-triazolo[1.5a]pyrimidine (2.5 g, 6.3 mmol, prepared according to WO-A 98/46608); dimethylformamide (15 ml), sodium hydride (0.25 g, 60%) and methyliodide is stirred at ambient temperature for 45 minutes. The reaction mixture is poured into watet (400 ml) and extracted with diethylether twice (300 ml). The organic Phase is separated, dried with anhydrous sodium sulphate and filtered. The filtrate is evaporated under reduced Pressure and purified by flash chromatography to yield 0.2 g of the product as a colorless oil.

Example 2-20

TABLE I (synthesized analogously to Ex. 1)

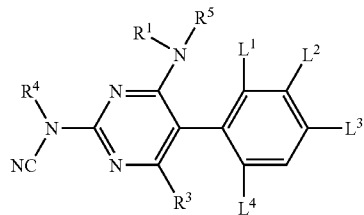

| Ex. | R$^1$ | R$^5$ | R$^6$ | L$^1$ | L$^2$ | L$^3$ | L$^4$ | melting point (° C.) |
|---|---|---|---|---|---|---|---|---|
| 2 | 1,1,1-trifluoro-prop-2-yl | H | butyl | F | H | F | F | 168–172 |
| 3 | iso-propyl | H | methyl | F | H | F | F | 130 |
| 4 | cyclopentyl | H | methyl | F | F | H | F | 140 |
| 5 | —(CH$_2$)$_2$—CH(CH$_3$)—(CH$_2$)$_2$— | | methyl | F | H | H | Cl | oil |
| 6 | 2-butyl | H | methyl | F | H | H | Cl | oil |
| 7 | —(CH$_2$)$_2$—CH(CH$_3$)—(CH$_2$)$_2$— | | methyl | F | H | F | F | 100 |
| 8 | 1,1,1-trifluoro-prop-2-yl | methyl | methyl | F | H | F | F | 86 |
| 9 | but-2-yl | ethyl | methyl | F | H | F | F | |
| 10 | norborn-2-yl | H | methyl | F | H | F | F | |
| 11 | —(CH$_2$)$_2$—CH(CH$_3$)—(CH$_2$)$_2$— | | ethyl | F | H | H | Cl | |
| 12 | cyclopentyl | H | methyl | F | H | F | F | |
| 13 | iso-propyl | H | methyl | F | H | H | Cl | |
| 14 | ethyl | ethyl | methyl | F | H | F | F | |
| 15 | 2,2,2-trifluoro-ethyl | H | methyl | F | H | F | F | |
| 16 | 1,1,1trifluoro-prop-2-yl | H | ethyl | F | | H | Cl | |
| 17 | 2-butyl | H | methyl | F | H | H | Cl | oil |
| 18 | norborn-2-yl | H | methyl | F | H | H | Cl | |
| 19 | 1,1,1-trifluoro-prop-2-yl | H | methyl | F | H | OCH$_3$ | F | |
| 20 | methyallyl | ethyl | methyl | F | H | F | F | |

TABLE I-continued (synthesized analogously to Ex. 1)

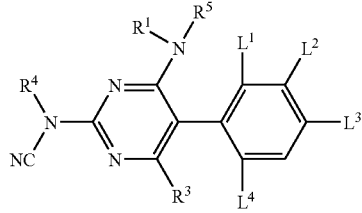

| Ex. | R¹ | R⁵ | R⁶ | L¹ | L² | L³ | L⁴ | melting point (° C.) |
|---|---|---|---|---|---|---|---|---|
| 21 | 2,2,2-trifluoro-ethyl | H | allyl | F | H | H | Cl | 177 |
| 22 | 1,1,1-trifluoro-prop-2-yl | H | n-propyl | F | H | F | F | 168–172 |
| 23 | —(CH₂)₇— | | methyl | H | F | H | F | oil |
| 24 | iso-propyl | methyl | methyl | F | H | H | Cl | oil |
| 25 | 1,1,1-trifluoro-prop-2-yl | H | methyl | F | H | F | F | oil |

Example 26

Preparation of 2-(N-cyano-N-methylamino)-4-chloro-5-(2,4,6-trifluorophenyl)-6-cyclohexylpyrimidine A mixture of 5-chloro-6-(2,4,6-trifluorophenyl)-7-cyclohexyltriazolo[1.5a]pyrimidine (2.5 g, 6.3 mmol, prepared according to WO-A 99/41255), dimethylformamide (15 ml), sodium hydride (0.25 g, 60%) and methyliodide is stirred at ambient temperature for 45 minutes. The reaction mixture is poured into water (400 ml) and extracted with diethylether twice (300 ml). The organic phase is separated, dried with anhydrous sodium sulphate and filtered. The filtrate is evaporated under reduced pressure and purified by flash chromatography to yield 0.2 g of the product as a colorless oil.

Example 27-39

TABLE II (synthesized analogously to Ex. 26)

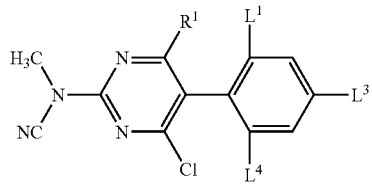

| Ex. | R¹ | L¹ | L³ | L⁴ | melting point (° C.) |
|---|---|---|---|---|---|
| 27 | n-heptyl | F | F | F | |
| 28 | cyclopentyl | F | F | F | |
| 29 | cyclohexyl | F | F | F | |
| 30 | 4-methylcyclohexyl | F | F | F | |
| 31 | 2-methylpropyl | F | F | F | |
| 32 | n-heptyl | F | F | Cl | |

TABLE II-continued (synthesized analogously to Ex. 26)

| Ex. | R¹ | L¹ | L³ | L⁴ | melting point (° C.) |
|---|---|---|---|---|---|
| 33 | cyclopentyl | F | H | Cl | |
| 34 | cyclohexyl | F | H | Cl | |
| 35 | n-hexyl | F | H | Cl | |
| 36 | 4-methylcyclohecyl | F | H | Cl | |
| 37 | 2-methylpropyl | F | H | Cl | |
| 38 | 4-fluorocyclohexyl | F | F | F | |
| 39 | 4-fluorocyclohexyl | F | OCH₃ | F | |

Example 40

Preparation of 4-chloro-2-(N-cyanoamino)-6-[(4-methyl)-piperidin-1-yl]-5-phenyl-pyrimidine To a solution of 4-chloro-6-[(4-methyl)-piperidin-1-yl]-2-methylsulfony-5-phenyl-pyrimidine (1.0 g, 2.7 mmol) in dimethylformamide (8 ml) at room temperature was added potassium carbonate (0.76 g, 5.47 mmol). After the reaction mixture had been stirred at room temperature for 17.5 hours the reaction mixture was then diluted with water (70 ml) and the resulting cloudy solution acidified to pH 1 by the addition of concentrated hydrochloric acid (4 ml). The resulting white suspension was then stirred at room temperature for 2 hours. The suspension was then filtered, washed with water followed by hexane and dried in vacuo overnight. The crude product was recrystalized from methylene chloride/hexane to afford 0.71 g (79% yield) of the title compound as a white crystalline solid (melting point: 219–220° C. (dec)).

Example 41

Preparation of 4-chloro-2-(N-cyano-N-methylamino)-6-[(4-methyl)-piperidin-1-yl]-5-phenylpyrimidine To a solution of 4-chloro-2-(N-cyanoamino)-6-[(4-methyl)-piperidin-1-yl]-5-phenylpyrimidine (0.1 g, 0.305 mmol) in dimethylformamide (4 ml) at room temperature was added water (2 ml) followed by potassium carbonate (0.084 g, 0.61 mmol) and the resulting suspension was warmed gently to afford a clear solution. To the cooled solution was then added methyl iodide (0.076 ml, 1.22 mmol) and the reaction mixture stirred at room temperature for 2.5 hours. The reaction was then quenched by the addition of saturated aqueous ammonium chloride solution (40 ml). After adding ethyl acetate (40 ml) the biphasic mixture was stirred for 5 minutes. The organic phase was then separated, washed with saturated brine (50 ml), dried over magnesium sulfate and concentrated in vacuo to afford a yellow syrup. The crude product was chromatographed an silica gel eluting with 90:10 v/v hexane: ethyl acetate to afford 0.09 g (87% yield) of the title compound as a colorless syrup.

Example 42

Preparation of 2-(N-benzyl-N-cyano)-4-chloro-6-[(4-methyl)-piperidin-1-yl]-5-phenylpyrimidine To a solution of 4-chloro-2-(N-cyanoamino)-6-[(4-methyl)-piperidin-1-yl]-5-phenyl-pyrimidine (0.37 g, 1.13 mmol) in dimethylformamide (10 ml) at room temperature was added water (3 ml) and potassium carbonate (0.19 g, 1.35 mmol). To the resulting milky suspension benzyl bromide (0.16 ml, 1.35 mmol) was added and stirred at room temperature for 18.75 hours before being quenched by the addition of a saturated aqueous ammonium chloride solution (40 ml). The mixture was then partitioned between ethyl acetate (75 ml) and water (75 ml), dried over magnesium sulfate and concentrated in vacuo to afford a yellow syrup. The crude product was chromatographed an silica gel eluting with 90:10 v/v hexane: ethyl acetate to afford 0.47 g (100% yield) of the title compound as a white crystalline solid (melting point 98–100° C.).

Example 43

Alternative Preparation of 4-chloro-2-(N-cyano-N-methylamino)-6-[(4methyl)-piperidin-1-yl]-5-phenylpyrimidine To a solution of 4-chloro-6-[(4-methyl)-piperidin-1-yl]-2-methylsulfonyl-5-phenyl-pyrimidine (0.5 g, 1.37 mmol) in dimethylformamide (6 ml) was added potassium carbonate (0.38 g, 2.73 mmol) followed by methyl cyanamide (0.31 g, 5.47 mmol). After stirring the reaction mixture at room temperature for 19 hours the reaction mixture was diluted with water (75 ml), and extracted with ethyl acetate (75 ml). The organic phase was washed with water (75 ml), followed by saturated brine (75 ml), dried over magnesium sulfate and concentrated in vacuo to afford a yellow syrup. The crude product was chromatographed an silica gel eluting with 90:10 v/v hexane: ethyl acetate to afford 0.39 g (84% yield) of the title compound as a colorless syrup.

Example 44

Preparation of the Starting Material 4-chloro-6-[(4-methyl)-piperidin-1-yl]-2-methylsulfonyl-5-phenylpyrimidine Step a: 5-Phenyl-2-methylthio-4,6(1H,5H)-pyrimidinedione 60.0 g (208 mmol) of ethyl 2-phenylmalonate and 19.0 g (249 mmol) of thiourea were heated at 150° C. for 2.5 hours in 77 g (416 mmol) of tri-n-butylamine. The resultant ethanol was for the most part distilled off. After the reaction solution had cooled, 180 ml of an aqueous solution of 24.9 g (623 mmol) of NaOH were added to it. After adding 50 ml of cyclohexane and stirring for about 30 min the aqueous phase was separated off, treated with 35.4 g (142 mmol) of methyl iodide and stirred at approximately 20 to 25° C. for about 16 h. After acidification with dilute HCl solution and stirring for about 30 min the precipitate was filtered off. After washing with water and drying, 16.7 g of the compound in the title (28% of theoretical) were obtained in the form of white crystals.

Step b: 4,6-Dichloro-5-phenyl-2-methylthiopyrimidine

A solution of 48.8 g (170 mmol) of the product from step A in 200 ml of phosphoryl chloride to which 3 ml of dimethylformamide (DMF) had been added was refluxed for 40 hours. After distilling off most of the phosphoryl chloride and diluting the residue with ethyl acetate, water was added while stirring at 15 to 20° C. After phase separation, the organic phase was washed with water and dilute NaBCO3 solution, then dried and freed of solvent. 37.5 g of the compound in the title (68% of theoretical) were obtained in the form of an oil which was employed in step C without further purification.

Step c: 6-Chloro-5-phenyl-4-[(4-methyl)piperidin-1-yl]-2-methylthiopyrimidine

A solution of 37.5 g (324 mmol) of the product from step B in 150 ml of anhydrous dichloromethane was treated with 24 g (406 mmol) of isopropylamine and stirred for five hours at about 20 to 25° C. The solvent was then distilled off, the residue taken up in ethyl acetate and washed with dilute HCl, water and dilute NaHCO$_3$ solution, then dried and freed of solvent. After chromatographing the residue on silica gel (cyclohexane/methyl tert-butyl ether 100:1 to 19:1) 13.4 g of the title compound (33% of theoretical) were obtained in the form of colorless crystals which were employed in the next stage without further purification.

Step d: Preparation of 6-chloro-4-[(4-methyl)-piperidin-1-yl]-2-methyl-sulfonyl-5 phenylpyrimidine A solution of 4-chloro-6-[(4-methyl)-piperidin-1-yl]-2-methylthio-5 phenylpyrimidine (17.19 g, 51.5 mmol) in methylene chloride (350 ml) was cooled to 0° C. After adding 70% in chloroperbenzoic acid (25.4 g, 103 mmol) the reaction mixture was stirred at 0° C. for 1 hour and at room temperature for 1.5 hours. The reaction mixture was then concentrated in vacuo to a small volume, diluted with ethyl acetate (400 ml), washed with 5% aqueous solution of sodium carbonate (3×300 ml) and saturated brine (300 ml), dried over magnesium sulfate and concentrated in vacuo to afford a white solid which was then recrystallized from ethyl acetate/hexane to afford 14.68 g (78% yield) of the title compound as an off-white crystalline solid (melting point: 160–162° C.).

Example 45

Preparation of the Intermediate 4-chloro-6-(N-cyclopentyl)amino-5-(2-fluorophenyl)-2-methylthiopyrimidine Step a: Preparation of 5-(2-fluorophenyl)-2-thiobarbituric Acid To absolute ethanol (200 ml), sodium (3.62 g, 157 mmol) was added at room temperature under nitrogen atmosphere. The reaction mixture was stirred until all the sodium had reacted. A solution of diethyl-(2-fluorophenyl)malonate (20 g, 78.7 mmol) in absolute ethanol (50 ml) was then added followed by thiourea (8.38 g, 110 mmol). The reaction mixture was then refluxed under nitrogen atmosphere for 17 hours. The cooled reaction mixture was then poured into water (800 ml), the reswiting mixture stirred for 15 minutes and extracted with diethyl ether (500 ml). The organic phase was extracted with brine (150 ml. 1/3 saturated) and the aqueous layers combined. Now concentrated hydrochloric acid (14 ml) was added to the aqueous phase and the resulting white suspension was stirred gently for 1 hour. The suspension was filtered and the resulting solid washed with water, followed by diethyl ether and dried in vacuo for approximately 12 hours to afford 8.59 g (46% yield) of the title compound as a white solid (melting point: >240° C.).

Step b: Preparation of 4,6-dihydroxy-5-(2-fluorophenyl)-2-methylthiopyrimidine

To a mixture of 5-(2-fluorophenyl)-2-thiobarbituric acid (8.20 g, 34.3 mmol) and a 2.0M aqueous solution of sodium hydroxide (68.5 ml, 13.8 mmol) was added dropwise over 30 minutes dimethyl sulfate (4.348, 34.4 mmol) at room temperature with stirring. The reaction mixture was stirred then for an additional 24 hours at room temperature. After washing with ethyl acetate (2×100 ml) the aqueous phase was acidified to pH 1 by adding concentrated hydrochloric acid (8 ml). The resulting white suspension was stirred for 30 minutes, filtered and the resulting white solid washed with water followed by hexane and dried under vacuum to afford 7.11 g of a white solid. Ethyl acetate (100 ml) was added to the crude product and the resulting suspension refluxed while stirring for 15 minutes. The cooled suspension was then filtered and dried to afford 5.41 g (615 yield) of the title compound as a white solid (m. p. >240° C.).

Step c: Preparation of 4,6-dichloro-5-(2-fluorophenyl)-2-methylthiopyrimidine

To a suspension of 4,6-dihydroxy-5-(2-fluorophenyl)-2-methylthiopyrimidine (0.75 g, 2.97 mmol) in phosphorous oxychloride (7.5 ml, 80.5 mmol) was added tri-n-propylamine (1.24 ml, 6.54 mmol) at room temperature under nitrogen atmosphere. After refluxing the reaction mixture for 18 hours and cooling to room temperature the reaction mixture was concentrated in vacuo and the resulting dark brown residue was dissolved in a minimum amount of acetonitrile and added to water (75 ml) under stirring. Ethyl acetate (75 ml) as then added and the resulting biphasic mixture stirred vigorously for one hour. The organic phase was separated, washed with 2M aqueous hydrochloric acid (75 ml), saturated aqueous sodium bicarbonate solution (2×75 ml) and saturated brine (75 ml). After drying over magnesium sulfate the organic Phase was concentrated in vacuo to afford a light brown oil. The crude product was chromatographed on silica gel eluting with 98:2 v/v hexane: ethyl acetate to afford 0.74 g (86% yield) of the title compound as colorless crystals.

Step d: Preparation of 4-chloro-6-(N-cyclopentyl)amino-5-(2-fluorophenyl)-2-methylthiopyrimidine To a solution of 4,6-dichloro-5-(2-fluorophenyl)-2-methylthiopyrimidine (0.74 g, 256 mmol) in methylene chloride (1 ml) at room temperature under nitrogen atmosphere was added cyclopentyl-amine (1.01 ml, 10.24 mmol) and the reaction mixture was stirred at room temperature for 15 hours. The reaction mixture was then diluted with 1:1 v/v diethyl ether ethyl acetate (75 ml), washed with 1 M aqueous hydrochloric acid (2×75 ml), saturated aqueous sodium bicarbonate solution (75 ml) and saturated brine (75 ml), dried over magnesium sulfate and concentrated in vacuo to afford a colorless syrup. The crude product was chromatographed on silica gel eluting with 95:5 v/v hexane: ethyl acetate to afford 0.87 g (100% yield) of the title compound as a white crystalline solid (melting point: 81–83° C.).

Example 46

Preparation of the Intermediate 4,6-dichloro-5-(2-chloro-6-fluorophenyl)-2-methylthiopyrimidine Step a: Preparation of 4,6-dihydroxy-5-(2-chloro-5-fluorophenyl)-2-methylthiopyrimidine A mixture of diethyl(2-chloro-6-fluorophenyl)malonate (12.01 g, 41.6 mmol), thiourea (3.8 g, 49.92 mmol) and tributylamine (19.82 ml, 83.2 mmol) was stirred at 150° C. under nitrogen atmosphere for 3 hours. The cooled reaction mixture was then partitioned between ethyl acetate (84 ml) and 2.0M sodium hydroxide solution (83.2 ml, 106 mmol) with vigorous stirring for 15 minutes. The aqueous phase was separated, dimethyl sulfate (5.258, 41.6 mmol) added and the mixture stirred for approximately 12 hours at room temperature. Additional 5.0 sodium hyroxide solution (33.4 ml, 166 mmol) and dimetylsulfate (2.63 g, 20.8 mmol) were added and the mixture stirred for further 2 hours. The resulting suspension was then filtered, the filtrate acidified to pH 1 by the addition of concentrated hydrochloric acid and stirred for 30 minutes. The resulting suspension was then filtered and the resulting white solid washed with water followed by hexane and dried under vacuum approximately 12 hours to afford 2.57 g (22% yield) of the title compound as a white solid.

Step b: Preparation of 4,6-dichloro-5-(2-chloro-6-fluorophenyl)-2-methylthiopyrimidine To a suspension of 4,6-dihydroxy-5-(2-chloro-6-fluorophenyl)-2-methylthiopyrimidine (2.57 g, 8.96 mmol) in phosphorous oxychloride (25.7 ml, 276 mmol) was added tri-n-propylamine (3.75 ml, 19.72 mmol) at room temperature under nitrogen atmosphere. After refluxing the reaction mixture at 140° C. for 40 hours and cooling to room temperature the reaction mixture was concentrated in vacuo to afford a black oil. The crude product was partitioned between ethyl acetate (250 ml) and water (250 ml) and the resulting biphasic mixture stirred vigorously for 15 minutes. The organic phase was separated, washed with 2M aqueous hydrochloric acid (2×250 ml), saturated sodium bicarbonate solution (2×250 ml) and saturated brine (250 ml). After drying over magnesium sulfate the organic Phase was concentrated in vacuo to afford 2.3 g (79% yield) of the title compound as a dark brown solid.

Examples 47-49

TABLE III (synthesized analogously to Ex. 40–46)

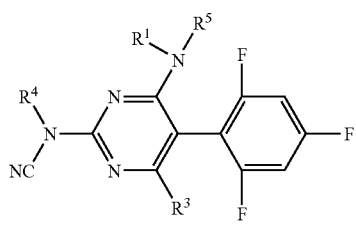

IA

| Ex. | $R^1$ | $R^5$ | $R^4$ | melting point (° C.) |
|---|---|---|---|---|
| 47 | $CF_3CH(CH_3)$ | H | $C_6H_5$—$CH_2$ | 178 |
| 48 | (S)-$CF_3CH(CH_3)$ | H | $CH_3O$—C($\!=\!$O)C($\!=\!$$CH_2$)$CH_2$ | 120–123 |
| 49 | $CF_3CH(CH_3)$ | H | $(CH_3CH_2O$—C[$\!=\!$O])$_2$C($CH_3$) | 178 |
| 50 | $CF_3CH(CH_3)$ | H | CH$\!\equiv\!$C—$CH_2$ | 185–186 |
| 51 | $CF_3CH(CH_3)$ | H | thien-3-yl-$CH_2$ | 68–72 |

Biological Investigations

A Determination of Minimum Inhibitory Concentration by Test Compounds in the Serial Dilution Test with *Pyricularia Oryzae*

The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 μg/ml. For preparation of the nutrient solution, V8 vegetable Juice (333 ml) is mixed with calcium carbonate (4.95 g), centrifuged, the supernatant (200 ml) diluted with water (800 ml) and autoclaved at 121° C. for 30 min.

The inocula of *Pyricularia Oryzae* are added into the wells as spore suspensions (50 μl; 5×10$^5$/ml) or agar slices (6 mm) of an agar culture of the fungus.

After 6–12 days incubation at temperatures of 18 to 25° C., the MIC values are determined by visual inspection of the plates, as shown in Table IV.

TABLE IV

| Example No. | MIC [μg/ml] |
|---|---|
| 3 | 3.13 |
| 4 | >100 |
| 5 | 25 |
| 6 | 6.25 |
| 7 | 100 |

B Evaluation of in vivo Fungicidal Activity of Test Compounds

Test compounds are dissolved in acetone and diluted with deionized water (95 parts water to 5 Parts acetone), containing 0.05% TWEEN 20®, a polyoxyethylene sorbitan monolaurate surfactant manufactured by Atlas Chemical Industries, to give a concentration of 200 ppm.

The plants are sprayed with the test solutions, dried and inoculated with fungi later the saure day. When disease symptom development is optimal, the plants are rated for disease control according to the rating scale shown below. Each test contains inoculated treated plants, inoculated untreated plants and inoculated plants treated with reference fungicides. The data obtained are shown in Table V.

Rating Scale

| Rating | Range % Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

Targets

| Symbol | Disease | Pathogen |
|---|---|---|
| AS | Apple Scab | *Venturia inaequalis* |
| RB | Rice Blast | *Pyricularia grisea* sp. *oryzae* |
| GDM | Grape downy mildew | *Uniclnula necator* |

TABLE V

| Example | AS | RB | GDM |
|---|---|---|---|
| 2 | 0 | 0 | 0 |
| 3 | 7 | 5 | 7 |
| 4 | 5 | 3 | 3 |
| 5 | 9 | 4 | 0 |
| 6 | 9 | 6 | 3 |

C Evaluation of in vitro Fungicidal Activity Against *Rhizoctonia solani*

Test compounds are dissolved in acetone to give a concentration of 10 ppm and added to individual cell walls (24-cell-well plates, Corning), which were previously filled with a suspension of ground fungal mycelium in a chemically defined growth medium. After 3–7 days of incubation, inhibition of mycelial growth is recorded using the following scale: The data obtained are shown in Table VI.

Rating Scale

| Rating | Degree of Inhibition |
|---|---|
| 0 | None |
| 3 | slight |
| 5 | moderate |
| 7 | severe |
| 9 | complete |

TABLE VI

| Example | Rhizoctonia solani (Rice sheath blight) |
| --- | --- |
| 1 | 7 |
| 4 | 7 |
| 5 | 0 |
| 6 | 0 |
| 7 | 0 |
| 8 | 7 |

The invention claimed is:

1. A process for the preparation of a pyrimidine of formula I

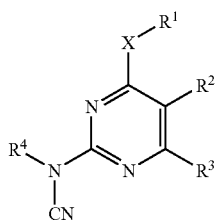

in which

R$^1$ represents C$_1$–C$_{10}$-alkyl, C$_1$–C$_{10}$-haloalkyl, C$_2$–C$_6$-alkenyl, C$_2$–C$_6$-alkynyl, C$_4$–C$_8$-alkadienyl, C$_1$–C$_{10}$-alkoxy, C$_3$–C$_8$-cycloalkyl, phenyl, tri-C$_1$–C$_6$-alkyl-silyl, formyl or C$_1$–C$_{10}$-alkoxy carbonyl, wherein R$^1$ groups are unsubstituted or substituted by one to three groups R$^a$;

R$^a$ is halogen, nitro, cyano, hydroxy, or is C$_1$–C$_{10}$-alkyl, C$_3$–C$_6$-cycloalkyl, C$_3$–C$_6$-cycloalkenyl, C$_1$–C$_{10}$-haloalkyl, C$_3$–C$_6$-halocycloalkyl, C$_1$–C$_{10}$-alkoxy, C$_1$–C$_{10}$-haloalkoxy, C$_1$–C$_{10}$-alkoxycarbonyl, tri-C$_1$–C$_4$-alkylsilyl, phenyl, halo- or dihalophenyl;

R$^2$ represents phenyl or C$_3$–C$_6$-cycloalkyl which are unsubstituted or substituted by one to three groups R$^a$;

R$^3$ represents hydrogen, halogen, or is C$_1$–C$_{10}$-alkyl, C$_1$–C$_{10}$-alkoxy, C$_1$–C$_{10}$-alkylthio, C$_1$–C$_{10}$-alkylamino or di-C$_1$–C$_{10}$-alkylamino, which are unsubstituted or substituted by one to three groups R$^a$;

R$^4$ represents C$_1$–C$_{10}$-alkyl, C$_2$–C$_6$-alkenyl or C$_2$–C$_6$-alkynyl; which are unsubstituted or substituted by one to three groups R$^a$; and X represents O, S, NR$^5$ or a single bond, wherein R$^5$ represents hydrogen, C$_1$–C$_{10}$-alkyl or C$_1$–C$_{10}$-haloalkyl; or R$^1$ and R$^5$ together with the interjacent nitrogen atom form a heterocyclic ring selected from the group consisting of pyrrolidine, piperidine, tetrahydropyridine and azepane, which ring is optionally substituted by one or more C$_1$–C$_{10}$-alkyl groups, which process comprises reacting a sulfone of formula VI

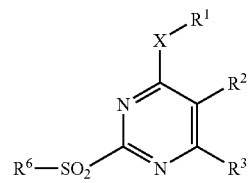

in which R$^6$ is C$_1$–C$_6$-alkyl or C$_1$–C$_6$-haloalkyl; with an alkylated cyanamide of formula VII

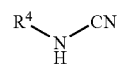

wherein the sulfone of formula VI is obtained by reacting a 2-thiopyrimidine compound of formula VIII

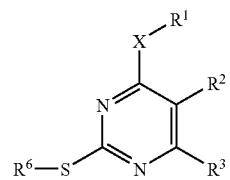

with an oxidizing agent.

2. The process of claim 1, in which R$^2$ of formulae I, VI and VIII represents a phenyl group of formula

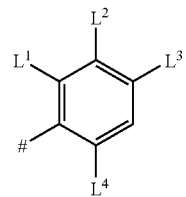

wherein L$^1$ through L$^4$ each independently represent hydrogen, fluorine, chlorine or methoxy.

3. The process of claim 1, in which X of formulae I, VI and VIII represents NR$^5$.

4. The process of claim 1, in which R$^3$ of formulae I, VI and VIII represents chlorine.

5. The process of claim 1, in which R$^4$ of formulae I and VII represents C$_1$–C$_6$-alkyl or benzyl.

6. A compound of formula VI or VIII

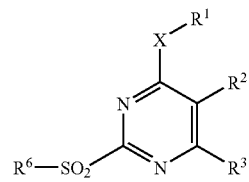

-continued

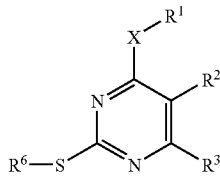

VIII wherein
- $R^1$ represents $C_1$–$C_{10}$-alkyl, $C_1$–$C_{10}$-haloalkyl, $C_2$–$C_6$-alkenyl, $C_2$–$C_6$-alkynyl, $C_4$–$C_8$-alkadienyl, $C_1$–$C_{10}$-alkoxy, $C_3$–$C_8$-cycloalkyl, phenyl, or
  - 5- or 6-membered heteroaryl or 5- or 6-membered heterocyclyl consisting of carbon ring members and heteroatoms as ring members, and containing as heteroatoms one to four nitrogen atoms or one to three nitrogen atoms and one sulfur or oxygen atom, or
  - tri-$C_1$–$C_6$-alkyl-silyl, formyl or $C_1$–$C_{10}$-alkoxycarbonyl; wherein $R^1$ groups are unsubstituted or substituted by one to three groups $R^a$
    - $R^a$ is halogen, nitro, cyano, hydroxy or
      - $C_1$–$C_{10}$-alkyl, $C_3$–$C_6$-cycloalkyl, $C_3$–$C_6$-cycloalkenyl, $C_1$–$C_{10}$-haloalkyl, $C_3$–$C_6$-halocycloalkyl, $C_1$–$C_{10}$-alkoxy, $C_1$–$C_{10}$-haloalkoxy, $C_1$–$C_{10}$-alkoxycarbonyl, tri-$C_1$–$C_4$-alkyl-silyl, phenyl, halo- or dihalophenyl or
      - 5- or 6-membered heteroaryl consisting of carbon ring members and heteroatoms as ring members, and containing as heteroatoms one to four nitrogen atoms or one to three nitrogen atoms and one sulfur or oxygen atom;
- $R^2$ represents phenyl which is unsubstituted or substituted by two or three groups $R^a$;
- $R^3$ represents chlorine;
- X represents $NR^5$, wherein $R^5$ represents hydrogen or $C_1$–$C_{10}$-alkyl or $C_1$–$C_{10}$-haloalkyl; or
- $R^1$ and $R^5$ together with the interjacent nitrogen atom form a heterocyclic ring selected from the group consisting of pyrrolidine, piperidine, tetrahydropyridine and azepane, which ring is optionally substituted by on or more $C_1$–$C_{10}$-alkyl groups; and
- $R^6$ represents $C_1$–$C_6$-alkyl or $C_1$–$C_6$-haloalkyl.

7. The compound of formula VI or VIII defined in claim 6, in which $R^2$ represents a phenyl group of formula

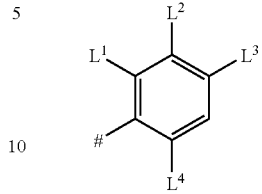

wherein $L^1$ through $L^4$ each independently represent hydrogen, fluorine, chlorine or methoxy.

8. The compound of formula VI defined in claim 6 which is represented by formula

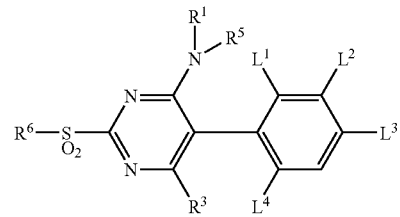

in which $L^1$ through $L^4$ each independently represent hydrogen, fluorine, chlorine or methoxy.

9. The compound of formula VIII defined in claim 6 which is represented by formula

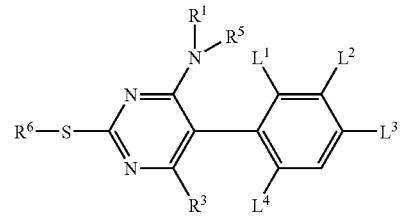

in which $L^1$ through $L^4$ each independently represent hydrogen, fluorine, chlorine or methoxy.

* * * * *

UNITED STATES PATENT AND TRADEMARK OFFICE
CERTIFICATE OF CORRECTION

| | | |
|---|---|---|
| PATENT NO. | : 7,230,104 B2 | Page 1 of 1 |
| APPLICATION NO. | : 11/186087 | |
| DATED | : June 12, 2007 | |
| INVENTOR(S) | : Pees et al. | |

It is certified that error appears in the above-identified patent and that said Letters Patent is hereby corrected as shown below:

In Claim 1, col. 25, indicated line 38:
"$C_1$-$C_{10}$alkoxy carbonyl" should read -- $C_1$-$C_{10}$-alkoxycarbonyl --

In Claim 6, col. 27, indicated line 31:
"5- or 6-membered heteroaryl consisting of" should read
--5- or 6-membered heteroaryl or 5- or 6-membered heterocyclyl, consisting of--

In Claim 6, col. 27, indicated line 40:
"hydrogen or" should read --hydrogen, --

Signed and Sealed this

Eighteenth Day of September, 2007

JON W. DUDAS
*Director of the United States Patent and Trademark Office*